US006465421B1

(12) United States Patent
Duranton et al.

(10) Patent No.: US 6,465,421 B1
(45) Date of Patent: *Oct. 15, 2002

(54) MODULATING BODY/CRANIAL HAIR GROWTH

(75) Inventors: Albert Duranton, Paris (FR); Olivier De Lacharriere, Paris (FR)

(73) Assignee: Societe l'Oreal S.A., Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/886,157

(22) Filed: Jun. 30, 1997

Related U.S. Application Data

(63) Continuation of application No. 08/322,198, filed on Oct. 13, 1994, now abandoned.

(30) Foreign Application Priority Data

Oct. 13, 1993 (FR) .............................................. 93 12178

(51) Int. Cl.⁷ ............................................... A61K 31/00
(52) U.S. Cl. ........................... 514/1; 514/169; 514/712; 514/715; 514/717; 514/880; 548/100; 562/400; 424/70.1; 554/1
(58) Field of Search ............................ 514/17–19, 169, 514/712, 715, 717, 880, 1; 548/100; 562/400; 424/70.1; 554/1

(56) References Cited

U.S. PATENT DOCUMENTS

| 4,274,974 A | * | 6/1981 | Kerkhoven .................. 252/90 |
| 4,370,315 A | | 1/1983 | Greff et al. ................... 424/94 |
| 4,686,231 A | | 8/1987 | Bender et al. ............... 514/333 |
| 4,847,270 A | | 7/1989 | Bender et al. ............... 514/333 |
| 4,973,474 A | * | 11/1990 | Hocquaux et al. ............ 424/70 |
| 5,002,941 A | | 3/1991 | Adams et al. .............. 514/186 |
| 5,037,655 A | * | 8/1991 | Giovanoni .................. 424/427 |
| 5,082,661 A | * | 1/1992 | Melnik ........................ 424/401 |
| 5,376,637 A | * | 12/1994 | Sawai et al. .................. 514/12 |
| 5,514,667 A | * | 5/1996 | Cullis-Hill .................... 514/54 |

FOREIGN PATENT DOCUMENTS

| FR | 2380775 | 9/1978 |
| WO | WO 94/27563 | 12/1994 |
| WO | WO 94/27586 | 12/1994 |

OTHER PUBLICATIONS

Sever, The Lancet 338, 1215, 1991.*
Bazzano, J. Am. Acad. Dermatol 15, 880–883, 1986.*
Contemporary Reviews In Obstetrics and Gynaecology, Apr. 1992, vol. 4, No. 22, pp. 90–101.
Journal Of The Pharmaceutical Society Of Japan, 1993, vol. 113, No. 10, pp. 718–724.
Journal Of Lipid Research, Sep. 1993, vol. 34, No. 9, pp. 1505–1514.
Edited by J.B. Harborne, "The Anthocyanins", *The Flavonoids*, 1988, pp. 1–5, Chapman and Hall Ltd., London, England.
Gabriel N. Hortobagyi et al., "Phase I Clinical Study of Nafazatrom", *Investigational New Drugs*, 1986; 4:251–255; Martinus Nijhoff Publishers, Boston, MA.
In re Kerkhoven, 205 USPQ 1069 (CCPA 1980).
SIGMA RBI Product Catalogue, Cell Signaling & Neuroscience, Signal Transduction Agents, Neurochemical, Antibodies, Kits, Cloned Receptors, and Peptides, 2000/2001, Vasoactive Intestinal Peptides, CAS No. 40077–57–4, p. 477.
"Orobol", ChemIDplus, National Institutes of Health, http://chem.sis.nlm.nih.gov/chemidplus/detail_sum.html?CompdID=000480239&page=names.
"Ebselen", ChemIDplus, National Institutes of Health, http://chem.sis.nlm.nih.gov/chemidplus/detail_sum.html?CompdID=060940343&page=names.
"Carnosol", ChemIDplus, National Institutes of Health, http://chem.sis.nlm.nih.gov/chemidplus/detail_sum.html?CompdID=005957802&page=names.
"Phenidone", ChemIDplus, National Institutes of Health, http://chem.sis.nlm.nih.gov/chemidplus/detail_sum.html?CompID=000092433&page=names.
"3–Indazolinone", ChemIDplus, National Institutes of Health, http://chem.sis.nlm.nih.gov/chemidplus/detail_sum.html?CompdID=007364252&page=names.
"Viprostol", ChemIDplus, National Institutes of Health, http://chem.sis.nlm.nih.gov/chemidplus/detail_sum.html?CompdID=073621928&page=names.
"Proxicromil", ChemIDplus, National Institutes of Health, http://chem.sis.nlm.nih.gov/chemidplus/detail_sum.html?CompdID=060400922&page=names.
"Vasoactive intestinal peptide", ChemIDplus, National Institutes of Health, http://chem.sis.nlm.nih.gov/chemidplus/detail_html?CompdID=037221797&page=names.

(List continued on next page.)

*Primary Examiner*—Christopher S. F. Low
*Assistant Examiner*—David Lukton
(74) *Attorney, Agent, or Firm*—Burns, Doane, Swecker & Mathis, L.L.P.

(57) ABSTRACT

The growth of body and/or head/cranial hair on mammalian organisms, for example humans, is modulated by administering thereto, whether topically and/or systemically, therapeutically effective amounts of at least one lipoxygenase or cyclooxygenase inhibitor, or at least one lipoxygenase or cyclooxygenase stimulator, preferably in the presence of at least one lipoxygenase/cyclooxygenase substrate or precursor thereof; when a hair-growth or hair loss-limiting response is sought to be elicited, a lipoxygenase inhibitor and/or cyclooxygenase stimulator is administered (conversely, to reduce or prevent hair growth, a lipoxygenase stimulator and/or cyclooxygenase inhibitor is administered).

1 Claim, No Drawings

OTHER PUBLICATIONS

"Lonapalene", 5595, Editor Susan Budavari et al., *The Merck Index An Encyclopedia of Chemicals, Drugs, and Biologicals*, 1996, 12th Edition, Merck Research Laboratories Division of Merck & Co., Inc. Whitehouse Station, NJ.

"Nordihydroguaiaretic Acid", 6786, Editor Susan Budavari et al., *The Merck Index An Encyclopedia of Chemicals, Drugs, and Biologicals*, 1996, 12th Edition, Merck Research Laboratories Division of Merck & Co., Inc. Whitehouse Station, NJ.

"Luteolin", 5641, Editor Susan Budavari et al., *The Merck Index An Encyclopedia of Chemicals, Drugs, and Biologicals*, 1996, 12th Edition, Merck Research Laboratories Division of Merck & Co., Inc. Whitehouse Station, NJ.

"Galangin", 4356, Editor Susan Budavari et al., *The Merck Index An Encyclopedia of Chemicals, Drugs, and Biologicals*, 1996, 12th Edition, Merck Research Laboratories Division of Merck & Co., Inc. Whitehouse Station, NJ.

"Boswellic Acid", 1382, Editor Susan Budavari et al., *The Merck Index An Encyclopedia of Chemicals, Drugs, and Biologicals*, 1996, 12th Edition, Merck Research Laboratories Division of Merck & Co., Inc. Whitehouse Station, NJ.

"Sulfasalazine", 9112, Editor Susan Budavari et al., *The Merck Index An Encyclopedia of Chemicals, Drugs, and Biologicals*, 1996, 12th Edition, Merck Research Laboratories Division of Merck & Co., Inc. Whitehouse Station, NJ.

"Zileuton", 10253, Editor Susan Budavari et al., *The Merck Index An Encyclopedia of Chemicals, Drugs, and Biologicals*, 1996, 12th Edition, Merck Research Laboratories Division of Merck & Co., Inc. Whitehouse Station, NJ.

"Ketoconazole", 5313, Editor Susan Budavari et al., *The Merck Index An Encyclopedia of Chemicals, Drugs, and Biologicals*, 1996, 12th Edition, Merck Research Laboratories Division of Merck & Co., Inc. Whitehouse Station, NJ.

"Itraconazole", 5262, Editor Susan Budavari et al., *The Merck Index An Encyclopedia of Chemicals, Drugs, and Biologicals*, 1996, 12th Edition, Merck Research Laboratories Division of Merck & Co., Inc. Whitehouse Station, NJ.

"Verapamil", 10083, Editor Susan Budavari et al., *The Merck Index An Encyclopedia of Chemicals, Drugs, and Biologicals*, 1996, 12th Edition, Merck Research Laboratories Division of Merck & Co., Inc. Whitehouse Station, NJ.

"Curcumin", 2744, Editor Susan Budavari et al., *The Merck Index An Encyclopedia of Chemicals, Drugs, and Biologicals*, 1996, 12th Edition, Merck Research Laboratories Division of Merck & Co., Inc. Whitehouse Station, NJ.

"Chlorogenic Acid", 2194, Editor Susan Budavari et al., *The Merck Index An Encyclopedia of Chemicals, Drugs, and Biologicals*, 1996, 12th Edition, Merck Research Laboratories Division of Merck & Co., Inc. Whitehouse Station, NJ.

"Esculin", 3739, Editor Susan Budavari et al., *The Merck Index An Encyclopedia of Chemicals, Drugs, and Biologicals*, 1996, 12th Edition, Merck Research Laboratories Division of Merck & Co., Inc. Whitehouse Station, NJ.

"Diethylcarbamazine", 3165, Editor Susan Budavari et al., *The Merck Index An Encyclopedia of Chemicals, Drugs, and Biologicals*, 1996, 12th Edition, Merck Research Laboratories Division of Merck & Co., Inc. Whitehouse Station, NJ.

"Baicalein", 971, Editor Susan Budavari et al., *The Merck Index An Encyclopedia of Chemicals, Drugs, and Biologicals*, 1996, 12th Edition, Merck Research Laboratories Division of Merck & Co., Inc. Whitehouse Station, NJ.

"Stanozolol", 8951, Editor Susan Budavari et al., *The Merck Index An Encyclopedia of Chemicals, Drugs, and Biologicals*, 1996, 12th Edition, Merck Research Laboratories Division of Merck & Co., Inc. Whitehouse Station, NJ.

(Abstract Only) SL Pfister et al., "Contribution of Arachidonic Acid Metabolites to Reduced Morepinephrine–Induced Contractions in Hypercholesterolemic Rabbit Aortas", *J Cardiovasc Pharmacol*, Dec. 1996; 28(6): 784–791.

(Abstract Only) B. Takase et al., "Arachidonic Acid Metabolites in Acute Myocardial Infarction", *Angiology*, Jul. 1996; 47(7): 649–661.

(Abstract Only) CS Foster et al., "Evidence for the Potential Influence of Cyclic Nucleotides on Maintenance of or Reactivation from Latency of herpes Simplex Virus in Trigeminal Ganglionic Neurons", *Acta Ophthalmol Suppl*, 1989; 192: 142–144.

(Abstract Only) G Neufang et al., "Abnormal differentiation of Epidermis in Transgenic Mice Constitutively Expressing Cyclooxygenase–2 in Skin", *Proc Natl Acad Sci USA*, Jun. 19, 2001; 98(13): 7629–7634.

(Abstract Only) PB Jacobson et al., "Fuscoside: An AntiInflammatory Marine Natural Product which Selectively Inhibits 5–Lipoxygenase. Part I: Physiological and Biochemical Studies in Murine Inflammatory Models", *J Pharmacol Exp Ther*, Aug. 1992: 262(2): 866–73.

(Abstract Only) PB Jacobson et al., "Fuscoside: An AntiInflammatory Marine Natural Product which Selectively Inhibits 5–Lipoxygenase. Part II: Biochemical Studies in the Human Neutrophil", *J Pharmacol Exp Ther*, Aug. 1992: 262(2): 874–82.

David Elfstrom, "Understanding NSAID–Induced Ulcers: How NSAIDs Work", elfstrom.com/atthritis/nsaids/actions.htm.

Muhammed Majeed, Ph.D., et al., "Ursolic Acid: Its Importance in Skin & Hair Beautification and Protection", www.sabinsa.com/products/ursolic–paper.htm.

"β–Boswellic Acid", 1382, Editor Susan Budavari et al., *The Merck Index An Encyclopedia of Chemicals, Drugs, and Biologicals*, 1996, 12th Edition, Merck Research Laboratories Division of Merck & Co., Inc., Whitehouse Station, NJ, USA.

"Borage Oil (*Borago officinalis*)", Vitamin Guide, http://www.gnc.com/health_notes/Supp/Borage.htm.

"Masoprocol", ACCESS Pharmaceuticals Inc. web page, http://informagen.com/Resource_Informagen/Deprecated/3025.html.

"Creosote bush (*Larrae tridentata*)", http://www.calflora.net/bloomingplants/creosotebush.html.

"Ginkgo biloba (*Ginkgoaceae ginkgo I.*)", The Ginkgo Pages, http://www.xs4all.nl/~kwanten/name.htm.

* cited by examiner

MODULATING BODY/CRANIAL HAIR GROWTH

This application is a continuation, of application Ser. No. 08/322,198, filed Oct. 13, 1994 now abandoned.

BACKGROUND OF THE INVENTION

1. Field of the Invention

The present invention generally relates to modifying the growth of body and/or head hair, and, more especially, to a treatment which, depending essentially on the nature of the compositions employed therefor, permits either promoting the growth and/or limiting the loss of body and/or head hair, or, contrariwise, reducing or preventing the growth of this hair.

The present invention also relates to such compositions, per se, and specific hair growth-modulating applications thereof.

2. Description of the Prior Art

It is known to the art that certain polyunsaturated fatty acids, in particular those containing 20 carbon atoms, such as arachidonic acid, dihomo-γ-linolenic acid, or, alternatively, eicosapentaenoic acid, may be converted, in vivo, under the action or influence of certain specific enzymes present in living cells, in particular in epithelial cells, into certain other compounds of eicosanoid type which are useful to the organism.

Thus, it too is known that the enzymes designated cyclooxygenases generate, from the various fatty acids indicated above, eicosanoids of prostaglandin and thromboxane type, and that the enzymes designated lipoxygenases are themselves responsible for the formation of eicosanoids of leukotriene type and other hydroxylated acyclic acids containing 20 carbon atoms. This same specific polyunsaturated fatty acid (or substrate) may initiate, depending on the nature of the enzyme with which it is first reacted, the formation of several different metabolites, for example prostaglandins and leukotrienes.

Polyunsaturated fatty acids, in particular $C_{20}$ acids (reactive starting materials), which are known to be metabolized under the specific action of the cyclooxygenase and lipoxygenase enzymes, are generally supplied to the living organism via certain foods, in particular certain natural oils of animal or vegetable origin. This food supply may either be in a direct form (which is, for example, the case for arachidonic acid, which is present as is in egg whites), or indirectly in the form of precursor compounds (compounds which are also deemed "essential fatty acids," themselves generally $C_{18}$–$C_{22}$ unsaturated fatty acids, such as linoleic acid, α-linolenic acid and γ-linolenic acid) which are converted via human metabolism, according to complex mechanisms which will not be repeated here, into suitable substrates (namely, metabolizable) for cyclooxygenases and lipoxygenases.

SUMMARY OF THE INVENTION

After considerable research efforts, it has now unexpectedly and surprisingly been found that the enzymatic conversions described above, and the various reaction products resulting therefrom, exert a significant influence on the mechanisms for the growth of body and/or head hair; thus, by favoring (according to techniques more fully described below) one or the other of the two cyclooxygenase or lipoxygenase enzymatic cascades in skin cells, it has now surprisingly been determined that the growth of body and/or head hair can be substantially modified.

Briefly, the present invention features promoting the growth of body and/or head hair and/or combatting the loss of such hair via cyclooxygenase treatment, as well as, contrariwise, retarding and/or preventing the growth of body/cranial hair via lipoxygenase treatment.

DETAILED DESCRIPTION OF BEST MODE AND PREFERRED EMBODIMENTS OF THE INVENTION

More particularly according to the present invention, from a practical standpoint, eliciting one or the other enzymatic response can be carried out via several different techniques, more fully described below. Each such technique is bottomed on the same basic principle, namely, to supply the organism, in particular the skin cells thereof, with compounds intended either to inhibit or, to the contrary, to stimulate the action or influence of cyclooxygenase or lipoxygenase enzymes, the selection of which obviously being made depending on the particular pharmacological effect sought to be attained.

Thus, if it is desired to promote the growth and/or to limit the loss of body and/or head hair (or conversely, if it is desired to retard and/or to prevent the growth of such hair), and taking account of the fact that it is appropriate, in this instance, as indicated above, to favor the cyclooxygenase route (or, conversely, to favor the lipoxygenase route), it is then possible to adopt, as desired, at least one of the following techniques: either employing one or more lipoxygenase inhibitors (or, conversely, one or more cyclooxygenase inhibitors), or employing one or more cyclooxygenase stimulators or agonists (or, conversely, one or more lipoxygenase stimulators or agonists), or employing one or more lipoxygenase inhibitors (or, conversely, one or more cyclooxygenase inhibitors) in combination with one or more cyclooxygenase stimulators or agonists (or, conversely, one or more lipoxygenase stimulators or agonists), or, alternatively, employing one or more active agents having the property of being both lipoxygenase inhibitors (or, conversely, cyclooxygenase inhibitors) and cyclooxygenase stimulators or agonists (or, conversely, lipoxygenase stimulators or agonists) simultaneously.

Stated differently, it is thus possible to elicit a given enzymatic response by direct stimulation of one particular route and/or via inhibition of the "contrary" route. The best results are typically attained by combining the two routes.

The present invention also features, both in a therapeutic regimen for promoting the growth of body and/or head hair and in a competing therapeutic regimen for limiting such hair growth, whether employing said inhibitors and stimulators or agonists of the aforesaid enzymatic routes, combining therewith treatment with at least one substrate which is directly metabolizable by lipoxygenases and cyclooxygenases and or with at least one precursor of said at least one substrate (synergistic or superadditive effect).

As utilized herein, by the term "substrate" suitable for lipoxygenase and cyclooxygenase is intended any substance which may be metabolized directly, as is in vivo, both by lipoxygenase enzymes and cyclooxygenase enzymes.

By the term lipoxygenase and cyclooxygenase substrate "precursor" is intended any substance which may be metabolized in vivo by the organism into a suitable substrate for lipoxygenases and cyclooxygenases, as well as any substance inducing the formation of polyunsaturated fatty acids in living tissues (this may be determined by gas chromatography or by any other standard technique, such as those described by Pelick et al, P23 "Analysis of lipids and lipoproteins", Perkin's American Oil Chemist Society editions, Champaign, Ill., U.S.A.).

By the term lipoxygenase and cyclooxygenase "inhibitor" is intended any substance which makes it possible, in vivo, to limit or to inhibit totally the enzymatic activity of one or the other of the aforesaid enzymes.

By the term lipoxygenase and cyclooxygenase "stimulator" or "agonist" is intended any substance which elicits, in vivo, an increase in the enzymatic activity of one or the other of these enzymes, the term "agonist" being included in the general designation "stimulator".

By "topical route" is intended any conventional technique for administration of an active agent by direct application thereof to a superficial (or external) parts of the body, such as skin, hair, etc.

And by "systemic route" is intended any conventional technique for administration of an active agent into the circulation via a route other than the topical route, for example, via the oral and/or parenteral route.

Thus, in a first embodiment of the present invention, an in vivo regimen is provided for modifying the growth of body and/or head hair, such regimen comprising administering to a mammalian organism, notably a human being, via a topical and/or systemic route, at least one lipoxygenase or cyclooxygenase inhibitor, or at least one lipoxygenase or cyclooxygenase stimulator or agonist.

In the event that the subject regimen/treatment is more particularly intended to promote the growth and/or to limit the loss of body and/or head hair, at least one active agent comprising a lipoxygenase inhibitor and/or a cyclooxygenase stimulator is employed.

In the event that the subject regimen/treatment is more particularly intended to retard and/or prevent the growth of body and/or head hair, at least one active agent comprising a lipoxygenase stimulator and/or a cyclooxygenase inhibitor is employed.

In a particularly preferred embodiment of the therapeutic regimen according to the invention, conjointly with said inhibitors or stimulators, at least one substrate for lipoxygenases and cyclooxygenases, or a precursor of said at least one substrate, is also administered to the organism. Administration of said substrate or of said precursor may then be carried out via a topical and/or systemic route, in a simultaneous or separate manner, or alternatively, in fractions over time, each relative to the administration of the lipoxygenase and cyclooxygenase inhibitors or stimulators.

In another embodiment of the present invention, special packages containing several compartments, or "kits," are used for carrying out the subject regimen, and in particular kits which comprise, in a first compartment, one or more lipoxygenase or cyclooxygenase inhibitors or one or more lipoxygenase or cyclooxygenase stimulators and, in a second compartment, one or more substrates for lipoxygenase and cyclooxygenase and/or one or more precursors of said one or more substrates. The compositions contained in said first and second compartments are thus considered combination compositions for simultaneous or separate use, or for use as separate fractions thereof over time, in a regimen for modulating the growth of body and/or head/cranial hair.

Thus, the present invention also features novel compositions or associations, per se, well suited for carrying out the various embodiments of the therapeutic regimen described above.

Next, the nature of the various active agents and compositions useful in the treatment of the present invention (inhibitor/stimulator/substrate/precursor) will be more fully described.

The inhibitory or stimulatory (or agonistic) activity of a given agent with respect to lipoxygenases or cyclooxygenases may easily be determined by one skilled in this art, in particular by means of the usual biochemical tests, generally based on chromatographic analyses. Thus, such activities may, for example, be determined via the following techniques or via any other standardized technique:

(a) Activity with respect to lipoxygenase 5, 12 and 15: exemplary is the technique comprising incubating a biological material (human polymorphonuclear leukocytes or hair) in the presence of C14 arachidonic acid or C14 linoleic acid; the hydroxy acids formed are extracted and separated by thin layer chromatography or HPLC chromatography (Vanderhoeck J. Y. and Bailey J. M. in J. Biol. Chem., 259, pp 6,752–6,761 (1984); Huang M. et al, Cancer Res., 51, pp 813–819 (1991); Baer A. N. and Green F. A. in J. Lipids Res., 34, pp 1,505–1,514 (1993); Ziboh V. A. et al in J. Invest. Dermatol., 83, pp 248–251 (1984);

(b) Activity with respect to lipoxygenase 5: exemplary are the spectrophotometric techniques described by Aharony D. and Stein R. L. in J. Biol. Chem., 261, pp 11,512–11,517 (1986), and by McMillan R. M. et al in Biochim. Biophys. Acta, 1005, pp 170–176 (1989);

(c) Activity with respect to cyclooxygenases: exemplary is the technique based on the use of a biological material (epidermis) incubated in the presence of C14 arachidonic acid; the hydroxy acids formed are extracted and separated by HPLC chromatography (Huang M. et al, Cancer Res., 51, pp 813–819 (1991) or identified by radioimmunoassays (Lysz T. W. and Needleman P. J., in Neurochim., 38, pp 1,111–1,117 (1982). Also exemplary is the test described in the article "Nitric Oxide Activates Cyclo-oxygenase Enzymes", by D. Salvameni et al, Proc. Natl. Sci. USA, Vol. 90, pp 7,240–7,244, August 1993.

The lipoxygenase inhibitors are advantageously selected from among the redox and non-redox inhibitors, redox inhibitor precursors, antioxidants, iron-chelating agents, imidazole-containing compounds, phenothiazines and benzopyran derivatives, as well as from certain eicosanoids.

The redox inhibitors may be selected from among catecholbutane derivatives (U.S. Pat. Nos. 5,008,294, 4,708, 964 and 4,880,637, such as nordihydroguaiaretic acid (NDGA) or one of the enantiomers thereof, such as masoprocol.

The redox inhibitors may also be selected from among phenidone, lonapalene, indazolinones, naphazatrom, benzofuranol, alkylhydroxylamine and the compounds of the following formulae:

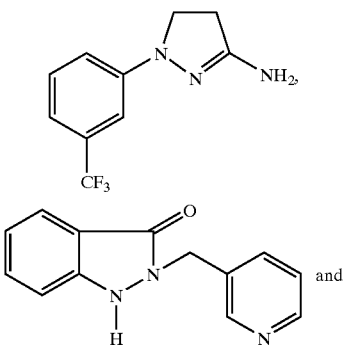

and

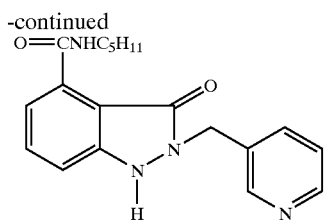

The non-redox inhibitors may be selected from among the hydroxythiazoles, methoxyalkylthiazoles, benzopyrans and derivatives thereof, methoxytetrahydropyran, boswellic acids and the acetyl derivatives thereof, and quinoline methoxyphenylacetic acids substituted with cycloalkyl radicals.

The antioxidant is advantageously selected from among the phenols, propyl gallate, flavonoids and natural compounds containing such flavonoids (Ginkgo biloba).

Exemplary flavonoids include the hydroxylated flavone derivatives such as flavonol, dihydroquercetin, luteolin, galangin and orobol. Also exemplary are the chalcone derivatives such as 4,2',4'-trihydroxychalcone, ortho-aminophenols, N-hydroxyureas, benzofuranols and ebselen, and active agents that enhance the activity of the reducing selenoenzymes.

The iron-chelating agent is advantageously selected from among the hydroxamic acids and derivatives thereof, N-hydroxyureas, 2-benzyl-1-naphthol, catechols, hydroxylamines, carnosol, naphthol, sulfasalazine, zileuton, 5-hydroxyanthranilic acid and 4-(ω-arylalkyl) phenylalkanoic acids.

The imidazole-containing compounds are preferably ketoconazole or itraconazole.

Exemplary eicosanoid inhibitors of lipoxygenases include octadecatetraenoic acid, eicosatetraenoic acid, docosapentenoic acid, eicosahexaenoic acid and docosahexaenoic acid and the various esters thereof, as well as various other eicosanoids, which may optionally be in ester form, such as $PGE_1$ (prostaglandin $E_1$), $PGA_2$ (prostaglandin $A_2$) viprostol, 15-monohydroxyeicosatetraenoic acid, 15-monohydroxyeicosatrienoic acid, 15-monohydroxy-eicosapentaenoic acid and leukotrienes B5, C5 and D5.

Various other compounds that inhibit lipoxygenases can also be used, for example active agents interfering with the flow of calcium, in particular phenothiazines and diphenylbutylamines, verapamil, fuscoside, curcumin, chlorogenic acid, caffeic acid, 5,8,11,14-eicosatetraynoic acid (ETYA), hydroyphenylretinamide, lanopalene, esculin, diethylcarbamazine, phenanthroline, baicalein, proxicromil, thioethers and in particular diallyl sulfide and di-(1-propenyl)sulfide.

The lipoxygenase stimulators themselves are advantageously selected from among the cytokines such as fibroblast growth factor (FGFβ), transforming growth factor (TGFβ) and epidermal growth factor (EGF).

The cyclooxygenase inhibitors are advantageously non-steroidal anti-inflammatory agents such as arylcarboxylic derivatives, pyrazole-containing derivatives, oxicam derivatives and nicotinic acid derivatives.

The cyclooxygenase stimulators or agonists are preferably selected from among the arachidonic acid metabolites, nitric oxide and nitric oxide-donating compounds, stanozolol, glutathione-donating compounds, neuropeptides and in particular vasoactive intestinal peptide (VIP), calcium, ionophores, anthocyanosides.

Lastly, an exemplary active agent which can serve as both a lipoxygenase inhibitor and as a cyclooxygenase stimulator is 6-chloro-2,3-dihydroxy-1,4-naphthoquinone (CDNQ).

With respect to suitable lipoxygenase and cyclooxygenase substrates, representative are the polyunsaturated fatty acids, in particular those containing 20 carbon atoms, such as arachidonic acid, dihomo-γ-linolenic acid, or, alternatively, eicosapentaenoic acid.

Particularly exemplary precursors of such substrates are the so-called essential polyunsaturated fatty acids such as linoleic acid, α-linolenic acid and γ-linolenic acid, as well as cell membrane phospholipids such as phosphatidylserine, phosphatidylethanolamine, phosphatidylcholine, phosphatidylinositol and diphosphatidylglycerol.

The above substrates or substrate precursors, in particular, may be obtained from certain natural compounds, in particular from certain foods, of animal, vegetable or microbial origin (vegetable oil extracts such as common evening primrose oil, borage oil, black currant seed oil, evening primrose oil, fish oil extracts and insect tissue oil extracts).

According to the present invention, such natural compounds which contain the desired substrates and/or the precursors of the desired substrates can be used directly. It is also possible to use materials produced by industrial synthesis.

It will also be appreciated that mixtures of inhibitors, mixtures of stimulators, mixtures of substrates and mixtures of precursors, as well and mixtures of these mixtures can be used equally as well, provided, of course, that these mixtures of mixtures remain compatible with the desired therapeutic response.

The regimen or therapeutic treatment according to the invention will now be more fully described.

As indicated above, the subject treatment process essentially comprises administering to a mammalian organism, via the topical and/or systemic route, at least one lipoxygenase or cyclooxygenase inhibitor, or at least one lipoxygenase or cyclooxygenase stimulator. Such administration is preferably conducted in combination (simultaneous, separate or in separate fractions over time) with administration of at least one substrate, or at least one substrate precursor, as described above.

The enzyme inhibitors and stimulators are preferably administered topically.

The substrates and/or the precursors thereof may themselves be administered either via the systemic route, and in this event, preferably via the oral route, or, even more preferably, via the topical route.

In a particularly preferred embodiment of the present invention, topically acceptable compositions containing enzyme inhibitors and/or stimulators on the one hand, in conjunction with the substrates and/or the precursors thereof on the other, are applied to the skin and/or the scalp.

It will be appreciated that all of the above compounds and compositions may be conventionally packaged in a form suiting the mode of administration or application intended (lotions, shampoos, tablets, syrups and the like), and whether or not including any topically or systemically pharmaceutically acceptable carrier or diluent therefor.

The compositions or "kits" according to the present invention include, in particular, the following:
  (i) compositions (A) comprising at least one lipoxygenase inhibitor and at least one cyclooxygenase stimulator;
  (ii) compositions (B) comprising at least one cyclooxygenase inhibitor and at least one lipoxygenase stimulator;
  (iii) compositions (C) comprising at least one lipoxygenase inhibitor and/or at least one cyclooxygenase stimulator, in combination with at least one substrate for lipoxygenases and cyclooxygenases and/or at least one precursor of such a substrate;

(iv) compositions (D) comprising at least one cyclooxygenase inhibitor and/or at least one lipoxygenase stimulator, in combination with at least one substrate for lipoxygenases and cyclooxygenases and/or at least one precursor of such a substrate;

(v) "kits" (E) comprising, in a first packet or compartment, at least one lipoxygenase inhibitor and, in a second packet or compartment, at least one cyclooxygenase stimulator;

(vi) "kits" (F) comprising, in a first packet or compartment, at least one cyclooxygenase inhibitor and, in a second packet or compartment, at least one lipoxygenase stimulator;

(vii) "kits" (G) comprising, in a first packet or compartment, at least one lipoxygenase inhibitor and/or at least one cyclooxygenase stimulator, or, conversely, at least one cyclooxygenase inhibitor and/or at least one lipoxygenase stimulator, and, in a second packet or compartment, at least one substrate for lipoxygenases and cyclooxygenases and/or at least one precursor of such a substrate.

Also as indicated above, each of the compositions (A), (B), (C) and (D), as well as each of the components in the compartments of the kits (E), (F) and (G), are conventionally packaged in a form suited for the various modes of administration or application envisaged therefor (lotions, shampoos, tablets, syrups, etc.). Thus, the compositions (A)–(D) and the kits (E)–(F) are preferably packaged in a form suitable for topical application and, in respect of the kits (G), the components of the first compartment are preferably packaged in a form adapted for topical application, whereas the components of the second compartment are packaged in a form adapted for oral administration.

In general, kits can be designed containing as many separate compartments as active agents (inhibitors, stimulators, substrates or substrate precursors) as desired or convenient to use.

The compositions or kits according to this invention, as well as the therapeutic regimen consistent therewith, may also include various conventional and usual additives and adjuvants, in particular cosmetics in the case of topical applications (in particular hair products), for example UV filters, thickening agents, penetrating agents such as urea, organic solvents such as ethanol and isopropanol, alkylene glycols, surface-active agents selected from among nonionic surfactants such as alkylpolyglycosides, cationic surfactants, anionic surfactants and amphoteric surfactants, dyes and pigments, anti-dandruff agents, perfumes and preservatives.

It is also possible to incorporate into the compositions according to the invention active agents having known activity in the field of body and/or head hair growth, for example such as 2,4-diamino-6-piperidinopyrimidine-3-oxide marketed under the trademark "Minoxidil" by Upjohn.

To attain appreciable effects, the frequency of administration or application of the compositions according to the invention, both with and without substrate or substrate precursor, is on the order of one to two times per day, for such prolonged period of time as is required to elicit the desired therapeutic response. In this regard, it should be appreciated that therapeutically effective amounts of inhibitors and or stimulators are, in general, quite low.

The present invention finds particularly useful applications in the field of treating various pathologies affecting the skin and/or the scalp, in particular hirsutism and alopecia, in particular iatrogenic alopecia.

In order to further illustrate the present invention and the advantages thereof, the following specific examples are given, it being understood that same are intended only as illustrative and in nowise limitative.

In said examples to follow, each reported composition was formulated and tested for its efficacy in modulating the growth of mammalian hair; also in said examples to follow, the term "no-rinse lotion" connotes a cranial hair formulation which need not be rinsed with water or the like after application thereof, while "rinse-lotion" connotes that a subsequent rinse with water or the like is indeed carried out.

EXAMPLE 1

No-Rinse Lotion

| Constituents | Amounts |
| --- | --- |
| NDGA | 0.1 g |
| Linoleic acid | 0.1 g |
| Propylene glycol | 22.8 g |
| 95° Ethanol | 55.1 g |
| Purified water | qs 100 g |

EXAMPLE 2

No-Rinse Lotion

| Constituents | Amounts |
| --- | --- |
| NDGA | 2 g |
| Linoleic acid | 5 g |
| Propylene glycol | 22.8 g |
| 95° Ethanol | 55.1 g |
| Purified water | qs 100 g |

EXAMPLE 3

Rinse Lotion

| Constituents | Amounts |
| --- | --- |
| NDGA | 5 g |
| Linoleic acid | 5 g |
| Propylene glycol | 22.8 g |
| 95° Ethanol | 55.1 g |
| Purified water | qs 100 g |

EXAMPLE 4

Rinse Lotion

| Constituents | Amounts |
| --- | --- |
| NDGA | 8 g |
| Linoleic acid | 15 g |
| Propylene glycol | 22.8 g |
| Absolute ethanol | qs 100 g |

EXAMPLE 5

| Shampoo | |
|---|---|
| Constituents | Amounts |
| NDGA | 1 g |
| Linoleic acid | 1 g |
| Surfactant APG 300 | 15 g |
|  | MA (= 30 g) |
| Purified water | qs 100 g |

EXAMPLE 6

| No-Rinse Lotion | |
|---|---|
| Constituents | Amounts |
| Ginkgo biloba[(1)] | 5 g |
| Propylene glycol | 22.8 g |
| 95° Ethanol | 55.1 g |
| Purified water | qs 100 g |

[(1)]flavonoid-rich natural extract

EXAMPLE 7

| No-Rinse Lotion | |
|---|---|
| Constituents | Amounts |
| Ketoconazole | 0.5 g |
| Propylene glycol | 22.8 g |
| 95° Ethanol | 55.1 g |
| Purified water | qs 100 g |

EXAMPLE 8

| No-Rinse Lotion | |
|---|---|
| Constituents | Amounts |
| Diallyl sulfide | 11.4 g |
| Propylene glycol | 22.8 g |
| 95° Ethanol | 55.1 g |
| Purified water | qs 100 g |

EXAMPLE 9

| No-Rinse Lotion | |
|---|---|
| Constituents | Amounts |
| Gingko biloba | 5 g |
| Linoleic acid | 5 g |
| Propylene glycol | 22.8 g |
| 95° Ethanol | 55.1 g |
| Purified water | qs 100 g |

EXAMPLE 10

| No-Rinse Lotion | |
|---|---|
| Constituents | Amounts |
| Ketoconazole | 0.5 g |
| Linoleic acid | 5 g |
| Propylene glycol | 22.8 g |
| 95° Ethanol | 55.1 g |
| Purified water | qs 100 g |

EXAMPLE 11

| No-Rinse Lotion | |
|---|---|
| Constituents | Amounts |
| Diallyl sulfide | 11.4 g |
| Linoleic acid | 5 g |
| Propylene glycol | 22.8 g |
| 95° Ethanol | 55.1 g |
| Purified water | qs 100 g |

EXAMPLE 12

| No-Rinse Lotion | |
|---|---|
| Constituents | Amounts |
| Ginkgo biloba | 5 g |
| Borage oil [(2)] | 10 g |
| Propylene glycol | 22.8 g |
| 95° Ethanol | 55.1 g |
| Purified water | qs 100 g |

[(2)]: natural extract containing 18:2n-6 and 18:3n-6 polyunsaturated fatty acids

EXAMPLE 13

| No-Rinse Lotion | |
|---|---|
| Constituents | Amounts |
| CDNQ | 2 g |
| Linoleic acid | 5 g |
| Propylene glycol | 22.8 g |
| 95° Ethanol | 55.1 g |
| Purified water | qs 100 g |

EXAMPLE 14

| No-Rinse Lotion | |
|---|---|
| Constituents | Amounts |
| CDNQ | 2 g |
| Borage oil | 10 g |
| Propylene glycol | 22.8 g |

-continued

No-Rinse Lotion

| Constituents | Amounts |
| --- | --- |
| 95° Ethanol | 55.1 g |
| Purified water | qs 100 g |

EXAMPLE 15

No-Rinse Lotion

| Constituents | Amounts |
| --- | --- |
| Indomethacin | 0.25 g |
| Propylene glycol | 22.8 g |
| 95° Ethanol | 55.1 g |
| Purified water | qs 100 g |

EXAMPLE 16

No-Rinse Lotion

| Constituents | Amounts |
| --- | --- |
| Indomethacin | 0.25 g |
| Docosahexaenoic acid | 2 g |
| Propylene glycol | 22.8 g |
| 95° Ethanol | 55.1 g |
| Purified water | qs 100 g |

All of the above compositions of Examples 1 to 14 demonstrated good results for the growth of mammalian head/cranial hair, in particular those containing a substrate or a substrate precursor for lipoxygenases and cyclooxygenases. The compositions of Examples 15 and 16 provided good results as regards the retardation of growth of mammalian body and head/cranial hair.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method of promoting hair growth comprising administering to a subject in need thereof a lipoxygenase inhibitor for a time and under conditions effective to promote hair growth, wherein said lipoxygenase inhibitor is selected from the group consisting of linoleic acid, nafazatrom, borage oil (isolated from *Borago officinalis*), Ginkgo biloba (isolated from the *Ginkgo biloba* tree), ketoconozole (cis-1-Acetyl-4-[4-[[2-(2,4-dichlorophenyl)-2-(1H-imidazol-1-ylmethyl)-1,3-dioxolan-4-yl]methoxy]phenyl]piperazine), diallyl sulfide, masoprocol (beta,gamma-Dimethyl-alpha,delta-bis (3,4-dihydroxyphenyl) butane, isolated from *Larrea tridentata*), benzofuranol, boswellic acid (($3\alpha,4\beta$)-3-hydroxyurs-12-en-23-oic acid, isolated from *Boswellia carterii*), flavenol, dihydroquercetin, luteolin (2-(3,4-Dihydroxyphenyl)-5,7-dihydroxy-4H-1-benzopyran-4-one, eicosahexaenoic acid, docosapentaenoic acid, galangin ((3,5,7-Trihydroxyflavone)) and docosahexaenoic acid.

* * * * *